(12) United States Patent
Sauer et al.

(10) Patent No.: US 8,344,171 B2
(45) Date of Patent: Jan. 1, 2013

(54) PROCESS FOR MAKING DIHYDROCARBYL HYDROCARBONPHOSPHONATES

(75) Inventors: Anne M. Sauer, Baton Rouge, LA (US); Techen Tsao, Baton Rouge, LA (US); Arthur G. Mack, Prairieville, LA (US); William J. Layman, Jr., Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 293 days.

(21) Appl. No.: 12/602,652

(22) PCT Filed: Jun. 5, 2008

(86) PCT No.: PCT/US2008/065858
§ 371 (c)(1),
(2), (4) Date: Dec. 1, 2009

(87) PCT Pub. No.: WO2008/154268
PCT Pub. Date: Dec. 18, 2008

(65) Prior Publication Data
US 2010/0179342 A1    Jul. 15, 2010

Related U.S. Application Data

(60) Provisional application No. 60/942,838, filed on Jun. 8, 2007.

(51) Int. Cl.
*C07F 9/40* (2006.01)
(52) U.S. Cl. .................................................. 558/114
(58) Field of Classification Search .................. 558/113
See application file for complete search history.

(56) References Cited

U.S. PATENT DOCUMENTS
2,754,319 A    7/1956    Johnston

FOREIGN PATENT DOCUMENTS
GB    2160872 A1    1/1986
WO    85/02849 A1    7/1985
WO    WO/85/02849    *    7/1985

OTHER PUBLICATIONS

Bailey, Nucleophilic addition-elimination reactions of N-(p-tolylsulfonyl)vinylsulfoximines: preparation of alpha-methylene nitriles and phosphonates, 1991, Tetrahedron Letters, vol. 32, No. 26, p. 3119-3122.*
Lambert, Participation of the beta phosphonate Group in Carbocation Formation, 1994, J. Org. Chem., vol. 59, p. 5397-5403.*
Gelman, D., et al., "Copper-Catalyzed C-P Bond Construction via Direct Coupling of Secondary Phosphines and Phosphites with Aryl and Vinyl Halides", Organic Letters, 2003, vol. 5, No. 13, pp. 2315-2318.
Han, Li-Biao, et al., "Efficient and Selective Nickel-Catalyzed Addition of H-P(O) and H-S Bonds to Alkynes", J. Am. Chem. Soc., 2004, vol. 126, No. 16, pp. 5080-5081.
Spears, Jr., L. Gene, et al., "Anionic Phosphorus as a Nucleophile. An Anion Chain Arbuzov Mechanism", J. Org. Chem., 1987, vol. 52, pp. 61-64.
Touil, S., et al., "Cetones Gamma-Phosphonatees: Synthese Et Etude Spectroscopique DE RMN DU 1H, DU 31P ET DU 13C", Journal de la Societe Chimique de Tunisie, vol. IV, No. 2, Dec. 1997, pp. 85-95.
Wilberg, K. B., et al., "Reactions of [1.1.1] Propellane", J. Am. Chem. Soc., 1990, vol. 112, pp. 2194-2216.

* cited by examiner

*Primary Examiner* — Golam M M Shameem
*Assistant Examiner* — Karen Cheng
(74) *Attorney, Agent, or Firm* — James A. Jubinsky

(57) ABSTRACT

This invention provides a process for the preparation of a dihydrocarbyl hydrocarbonphosphonate. The process comprises forming a reaction mixture from components comprising (i) at least one dihydrocarbyl phosphite, (ii) at least one alkali metal hydrocarbyloxide, and (iii) at least one alcohol, so that a dihydrocarbyl hydrocarbonphosphonate is formed.

13 Claims, No Drawings

PROCESS FOR MAKING DIHYDROCARBYL HYDROCARBONPHOSPHONATES

REFERENCE TO RELATED APPLICATIONS

This application is the National Stage of International Patent Appl. No. PCT/US2008/065858, filed on Jun. 5, 2008, which in turn claims the benefit of U.S. Provisional Patent Appl. No. 60/942,838, filed on Jun. 8, 2007, the disclosures of which are incorporated herein by reference.

TECHNICAL FIELD

This invention relates to a novel and efficient method for the formation of dihydrocarbyl hydrocarbonphosphonates.

BACKGROUND

A conventional approach to generate phosphonates relies on the Michaelis-Arbuzov rearrangement. This reaction is one of the most extensively investigated and well-known reactions in organic chemistry. First discovered by Michaelis in 1898, this reaction has provided an efficient and direct entry into phosphonate systems.

Specifically, the formation of dihydrocarbyl hydrocarbonphosphonates in the Michaelis-Arbuzov rearrangement relies on the reaction of a trialkyl phosphite with an alkyl halide in the presence of a transition metal salt as a catalyst. Today, many commercially available phosphonate chemicals are made with this technology, including dimethyl methanephosphonate. However, this methodology presents problems in its current practice. In some instances, this reaction is economically infeasible due to the required use of alkyl halides and the transition metal catalysts. Additionally, environmental concerns, such as ozone depletion, may be raised by this method of producing phosphonates. Further, these reactions often require temperatures in excess of 100° C., and tend to be exothermic in nature. It would be desirable if a new way could be found to produce dihydrocarbyl hydrocarbonphosphonates which minimizes without the problems or shortcomings just described.

SUMMARY OF THE INVENTION

A process for preparing dihydrocarbyl phosphonates has been discovered, which process minimizes or eliminates many, if not all, of the detrimental effects of the Michaelis-Arbuzov rearrangement referred to above. Advantageously, the processes of this invention can be conducted in a single reactor, thus reducing process time and conserving economic resources.

In one of its embodiments, this invention provides a process for the preparation of a dihydrocarbyl hydrocarbonphosphonate, which process comprises forming a reaction mixture from components comprising (i) at least one dihydrocarbyl phosphite, (ii) at least one alkali metal hydrocarbyloxide, and (iii) at least one alcohol, so that dihydrocarbyl hydrocarbonphosphonate is formed.

The above and other embodiments will be apparent from the ensuing description and the appended claims.

FURTHER DETAILED DESCRIPTION OF THE INVENTION

As used throughout this document, the term "hydrocarbyl" includes an alkyl, aryl, alkaryl, aralkyl, alkenyl, cycloalkyl or cycloalkenyl group. The alkyl and alkenyl groups can be linear or branched. Throughout this document, the term "alcohol" is used to include alcohols in which the hydroxy group is attached to an alkyl, aryl, alkaryl, aralkyl, alkenyl, cycloalkyl or cycloalkenyl group. The dihydrocarbyl phosphites used in the processes of this invention are more correctly called dihydrocarbyl hydrogen phosphites; thus, as used throughout this document, the term "dihydrocarbyl phosphite" and any such specific dihydrocarbyl phosphites (e.g., dimethyl phosphite) are to be understood to mean dihydrocarbyl hydrogen phosphites (e.g., dimethyl hydrogen phosphite).

As stated above, this invention provides processes for the preparation of dihydrocarbyl hydrocarbonphosphonates, which process comprises forming a reaction mixture from components comprising (i) at least one dihydrocarbyl phosphite, (ii) at least one alkali metal hydrocarbyloxide, and (iii) at least one alcohol, so that a dihydrocarbyl hydrocarbonphosphonate is formed. More particularly, the product of the processes of this invention is one or more compounds of the formula $$RP(O)(OR^1)(OR^2)$$

where R, $R^1$, and $R^2$ are the same or different, and each is a hydrocarbyl group. In the naming of these compounds, $R^1$ and $R^2$ in the above formula are the dihydrocarbyl groups of the dihydrocarbyl hydrocarbonphosphonate, and are bound to phosphorus by ester linkages. R is directly bonded to phosphorus. Although R is a hydrocarbyl group, R in the above formula is named as a hydrocarbon group in the dihydrocarbyl hydrocarbonphosphonate, to distinguish it from the ester-linked groups $R^1$ and $R^2$. For example, when R is a methyl group, the dialkyl hydrocarbonphosphonate is called a dialkyl methanephosphonate, or when R is a phenyl group, the dialkyl hydrocarbonphosphonate is called a dialkyl benzenephosphonate.

Thus, in the processes of this invention, without wishing to be bound by theory, the overall reaction that is believed to occur can be represented by the following equation:

$$HP(O)(OR^1)(OR^2) + AOR \rightarrow RP(O)(OR^1)(OR^2)$$

where A is an alkali metal, R, $R^1$, and $R^2$ are the same or different, and each is a hydrocarbyl group. When R, $R^1$, and $R^2$ are the same, the reaction appears to proceed as shown in the above equation. When at least one of R, $R^1$, and $R^2$ is different than the other two of R, $R^1$, and $R^2$, transesterification occurs and a mixture of products is obtained, e.g., $R^1P(O)(OR)(OR^2)$ and $R^2P(O)(OR)(OR^1)$ in addition to $RP(O)(OR^1)(OR^2)$. A different result is obtained when an aryl phosphite, such as diphenyl phosphite, is reacted with an alkali metal hydrocarbyloxide which is an alkoxide: all of the aryl groups on the phosphite are replaced by alkyl groups.

In the process for the preparation of dihydrocarbyl hydrocarbonphosphonate, at least one dihydrocarbyl phosphite is used to form the reaction mixture. The hydrocarbyl groups of the dihydrocarbyl phosphite can be the same or different, but are preferably the same. Generally, the hydrocarbyl groups of the dihydrocarbyl phosphite have one to about thirty carbon atoms. Preferred alkyl groups for the dihydrocarbyl phosphite have one to about six carbon atoms. Preferred alkenyl groups for the dihydrocarbyl phosphite have about four to about ten carbon atoms. Preferred aralkyl groups for the dihydrocarbyl phosphite have seven to about twelve carbon atoms. Preferred aryl groups for the dihydrocarbyl phosphite have six to about fifteen carbon atoms. Preferably, both of the hydrocarbyl groups of the dihydrocarbyl phosphite are alkyl groups.

Examples of dihydrocarbyl phosphites that can be used in this invention include, but are not limited to, dimethyl phosphite, diethyl phosphite, methyl ethyl phosphite, dipropyl phosphite, methyl propyl phosphite, dibutyl phosphite, dipentyl phosphite, dicyclopentyl phosphite, dihexyl phosphite, dicyclohexyl phosphite, dibutenyl phosphite, dipentenyl phosphite, dibenzyl phosphite, di(4-methylbenzyl) phosphite, diphenyl phosphite, ditolyl phosphite, dinaphthyl phosphite, and the like. Preferred dihydrocarbyl phosphites include dimethyl phosphite and diethyl phosphite. Mixtures of two or more dihydrocarbyl phosphites can be used; a mixture of products will be obtained.

For the alkali metal hydrocarbyloxide, the alkali metal is usually lithium, sodium, or potassium, and preferably is sodium or potassium. The hydrocarbyl portion of the alkali metal hydrocarbyloxide is preferably an alkyl, alkenyl, or aralkyl group. When the hydrocarbyl portion of the alkali metal hydrocarbyloxide is an alkyl group, it preferably has from one to about six carbon atoms. When the hydrocarbyl portion of the alkali metal hydrocarbyloxide is an alkenyl group, it preferably has from about four to about ten carbon atoms. When the hydrocarbyl portion of the alkali metal hydrocarbyloxide is an aryl group, it preferably has from six to about fifteen carbon atoms. When the hydrocarbyl portion of the alkali metal hydrocarbyloxide is an aralkyl group, it preferably has from seven to about fifteen carbon atoms. Mixtures of two or more alkali metal hydrocarbyloxides can be used in the practice of this invention.

Suitable alkali metal hydrocarbyloxides in which the hydrocarbyl portion is an alkyl or cycloalkyl group include lithium methoxide, sodium methoxide, potassium methoxide, lithium ethoxide, sodium ethoxide, potassium ethoxide, lithium n-propoxide, sodium n-propoxide, potassium n-propoxide, lithium isopropoxide, sodium is opropoxide, potassium isopropoxide, lithium cyclopropanoxide, sodium cyclopropanoxide, potassium cyclopropanoxide, lithium n-butoxide, sodium n-butoxide, potassium n-butoxide, lithium sec-butoxide, sodium sec-butoxide, potassium sec-butoxide, lithium tert-butoxide, sodium tert-butoxide, potassium tert-butoxide, lithium cyclobutanoxide, sodium cyclobutanoxide, potassium cyclobutanoxide, lithium pentanoxide, sodium pentanoxide, potassium pentanoxide, lithium cyclopentanoxide, sodium cyclopentanoxide, potassium cyclopentanoxide, lithium hexanoxide, sodium hexanoxide, potassium hexanoxide, lithium cyclohexanoxide, sodium cyclohexanoxide, potassium cyclohexanoxide, lithium heptanoxide, sodium heptanoxide, potassium heptanoxide, lithium cycloheptanoxide, sodium cycloheptanoxide, potassium cycloheptanoxide, lithium octanoxide, sodium octanoxide, potassium octanoxide, lithium cyclooctanoxide, sodium cyclooctanoxide, potassium cyclooctanoxide, and the like.

Suitable alkali metal hydrocarbyloxides in which the hydrocarbyl portion is unsaturated (alkenyl, cycloalkenyl, aryl, or aralkyl) include lithium 2-buten-1-oxide, sodium 2-buten-1-oxide, potassium 2-buten-1-oxide, lithium 3-penten-1-oxide, sodium 3-penten-1-oxide, potassium 3-penten-1-oxide, lithium 3-hexen-1-oxide, sodium 3-hexen-1-oxide, potassium 3-hexen-1-oxide, lithium 2-cyclohexen-1-oxide, sodium 2-cyclohexen-1-oxide, potassium 2-cyclohexen-1-oxide, lithium phenoxide, sodium phenoxide, potassium phenoxide, lithium methylphenoxide, sodium methylphenoxide, potassium methylphenoxide, lithium dimethylphenoxide, sodium dimethylphenoxide, potassium dimethylphenoxide, lithium ethylphenoxide, sodium ethylphenoxide, potassium ethylphenoxide, lithium 2-naphthoxide, sodium 2-naphthoxide, potassium 2-naphthoxide, lithium 2-methyl-1-naphthoxide, sodium 2-methyl-1-naphthoxide, potassium 2-methyl-1-naphthoxide, lithium benzoxide, sodium benzoxide, potassium benzoxide, lithium 4-methylbenzoxide, sodium 4-methylbenzoxide, potassium 4-methylbenzoxide, lithium 4-ethylbenzyoxide, sodium 4-ethylbenzyoxide, potassium 4-ethylbenzyoxide, lithium 2-phenylethoxide, sodium 2-phenylethoxide, potassium 2-phenylethoxide, lithium 3-methylphenethoxide, sodium 3-methylphenethoxide, potassium 3-methylphenethoxide, lithium 1,1-diphenylethoxide, sodium 1,1-diphenylethoxide, potassium 1,1-diphenylethoxide, lithium 1-naphthalenemethoxide, sodium 1-naphthalenemethoxide, potassium 1-naphthalenemethoxide, lithium 2-naphthalenemethoxide, sodium 2-naphthalenemethoxide, potassium 2-naphthalenemethoxide, lithium 6-methyl-2-naphthalenemethoxide, sodium 6-methyl-2-naphthalenemethoxide, potassium 6-methyl-2-naphthalenemethoxide, lithium 1-naphthalenethoxide, sodium 1-naphthalenethoxide, potassium 1-naphthalenethoxide, lithium 2-naphthalenethoxide, sodium 2-naphthalenethoxide, potassium 2-naphthalenethoxide, and the like.

Preferred alkali metal hydrocarbyloxides in the practice of this invention include sodium methoxide, sodium ethoxide, and sodium benzoxide.

Normally, the alcohol corresponds to the hydrocarbyloxide portion of the alkali metal hydrocarbyloxide, i.e., the hydrocarbyloxide portion of the alkali metal hydrocarbyloxide is the same as the hydrocarbyl portion of the alcohol. For example, when the alkali metal hydrocarbyloxide is sodium methoxide, the alcohol is usually methanol. The alkali metal hydrocarbyloxide is generally used as a solution in the corresponding alcohol. If desired, when conducting the processes of this invention, additional alcohol can be employed. Normally and preferably, any additional alcohol is the same alcohol as that which corresponds to the alkali metal hydrocarbyloxide.

The alcohol is a hydrocarbyl alcohol, and is preferably a liquid alcohol. When the alcohol is not liquid at the conditions under which the reaction is conducted, elevated temperatures and/or increased pressure can be used to liquefy the alcohol. If such conditions are not used to liquefy the alcohol, a solvent may be used to provide the alcohol in the liquid phase.

For the alcohol, the hydrocarbyl portion is preferably an alkyl, alkenyl, or aralkyl group. When the hydrocarbyl portion of the alcohol is an alkyl group, it preferably has from one to about six carbon atoms. When the hydrocarbyl portion of the alcohol is an alkenyl group, it preferably has from about four to about ten carbon atoms. When the hydrocarbyl portion of the alcohol is an aryl group, it preferably has from six to about fifteen carbon atoms. When the hydrocarbyl portion of the alcohol is an aralkyl group, it preferably has from seven to about fifteen carbon atoms. When a mixture of two or more alcohols is used, a mixture of alkali metal hydrocarbyloxides, and thus a mixture of products, results.

Examples of alcohols that can be used in the processes of this invention include, but are not limited to, methanol, ethanol, n-propanol, isopropanol, n-butanol, cyclopropanol, isobutanol, tert-butanol, cyclobutanol, pentanol, cyclopentanol, cyclohexanol, heptanol, cycloheptanol, octanol, cyclooctanol, 2-buten-1-ol, 3-penten-1-ol, 3-hexen-1-ol, 2-cyclohexen-1-ol, phenol, methylphenol, dimethylphenol, ethylphenol, 2-naphthol, 2-methyl-1-naphthol, benzyl alcohol, 4-methylbenzyl alcohol, 4-ethylbenzyl alcohol, 2-phenylethanol, 3-methylphenethyl alcohol, 1,1-diphenylethanol, 3-methylphenethyl alcohol, 1-naphthalenemethanol, 2-naphthalenemethanol, 6-methy1-2-naphthalenemethanol, 1-naphthalenethanol, and 2-naphthalenethanol. Methanol, ethanol, and benzyl alcohol are preferred liquid alcohols.

Typically, the mole ratio of alkali metal hydrocarbyloxide to dihydrocarbyl phosphite is at least about 0.75:1, and preferably is in the range of about 0.9:1 to about 1.5:1. The use of excess alkali metal hydrocarbyloxide relative to dihydrocarbyl phosphite is preferred.

The alcohol is generally used in an amount that is at least sufficient to keep all of the components of the reaction mixture in solution. When the amount of alcohol is small, the concentration of alkali metal hydrocarbyloxide is higher, and in such instances, the alkali metal hydrocarbyloxide should be added with greater caution (e.g., at a slower rate). Generally, the alcohol is present in an amount that is about 70 wt % to about 90 wt % relative to the alkali metal hydrocarbyloxide (i.e., the alkali metal hydrocarbyloxide is about 10 wt % to about 30 wt % solution in the alcohol). Very large amounts of alcohol minimize heat releases from the reaction, but can be a hindrance if it becomes necessary to add heat to the reaction.

An inert environment in which the presence of moisture and oxygen are minimized is employed in the processes of this invention because of the sensitivity of at least the alkali metal hydrocarbyloxide to moisture and oxygen. The presence of an inert atmosphere comprised of one or more inert gases, such as, for example, nitrogen, helium, or argon during the processes of this invention is preferred.

A recommended way of combining the components to form a reaction mixture is to add the alkali metal hydrocarbyloxide in alcohol (usually the corresponding alcohol) to the dihydrocarbyl phosphite. The addition of the alcoholic alkali metal hydrocarbyloxide solution can begin before all of the dihydrocarbyl phosphite is present, although it is usually recommended and preferred that the alkali metal hydrocarbyloxide solution is added after all of the dihydrocarbyl phosphite is present in the reaction zone, to help minimize the exotherm associated with the addition of the alkali metal hydrocarbyloxide solution. A rate of addition of alkali metal hydrocarbyloxide solution that prevents an excessive exotherm is such that the amount of heat produced can be kept under control, i.e., no uncontrolled heat release occurs. It is to be understood that the rate at which the alkali metal hydrocarbyloxide solution is added will vary with the scale of the reaction and the method used for removing heat from the reaction zone.

As the alkali metal hydrocarbyloxide solution is added to the dihydrocarbyl phosphite, the temperature initially increases, and cooling of the reaction zone is sometimes necessary. As the addition of alkali metal hydrocarbyloxide progresses, the temperature in the reaction zone often decreases, and at least at this stage, it is desirable to heat the reaction mixture, generally to a temperature high enough to drive the reaction as far as possible toward completion. Progress of the reaction can be monitored spectroscopically, e.g., by $^{31}$P NMR.

On the laboratory scale, reaction times are typically about four to about five hours. The reaction time can be shortened by operating at increased temperatures.

After formation, the dihydrocarbyl hydrocarbonphosphonate can be separated from the reaction mixture by conventional means, such as filtration and/or distillation. The distillation process can be repeated to improve the purity of the separated components.

As alluded to above, the products of the processes of this invention are dihydrocarbyl hydrocarbonphosphonates. Thus, the hydrocarbyl groups of the dihydrocarbyl hydrocarbonphosphonate usually have one to about thirty carbon atoms; preferred alkyl and alkenyl groups for the dihydrocarbyl hydrocarbonphosphonate have one to about six carbon atoms; preferred aralkyl groups for the dihydrocarbyl hydrocarbonphosphonate have seven to about twelve carbon atoms; and preferred aryl groups for the dihydrocarbyl hydrocarbonphosphonate have six to about fifteen carbon atoms. Preferably, both of the hydrocarbyl groups of the dihydrocarbyl phosphonate are alkyl groups. More preferably, both of the hydrocarbyl groups of the dihydrocarbyl phosphonate are alkyl groups, and the hydrocarbon is an alkane. Preferred products of the processes of this invention are dimethyl methanephosphonate, diethyl ethanephosphonate, dimethyl ethanephosphonate, dimethyl allenephosphonate, diethyl allenephosphonate, dimethyl benzenephosphonate, diethyl benzenephosphonate, and the like.

The following examples are presented for purposes of illustration, and are not intended to limit, and should not be construed as limiting, the scope of this invention.

EXAMPLE 1

A three-neck, 100 mL round-bottom flask, fitted with a thermometer, reflux condenser, and a septum, was charged with dimethyl phosphite (32 g, 0.29 mol). A solution of sodium methoxide (25 wt % in methanol, 62.8 g, 0.29 mol) was cautiously injected dropwise while maintaining the contents of the flask at 85° C. The sodium methoxide solution was added at a rate that maintained the temperature in the flask at about 85° C. The mixture was stirred at reflux while monitoring the reaction progress via NMR ($^1$H and $^{31}$P; product $^{31}$P NMR: δ=34.99 ppm; m/z=124.9). When the reaction was complete, the phosphonate product, dimethyl methylphosphonate, was isolated via distillation. The distilled product was characterized via gas chromatography-mass spectrometry (GC-MS).

EXAMPLE 2

A three-neck, 100 mL round-bottom flask, fitted with a thermometer, reflux condenser, and a septum, was charged with diethyl phosphite (35 g, 0.25 mol). A solution of sodium methoxide (25 wt % in methanol, 73 g, 0.338 mol, 1.3 equiv. relative to phosphite) was cautiously injected dropwise while maintaining the contents of the flask at 85° C. The mixture was stirred reflux while monitoring the reaction progress via NMR ($^1$H and $^{31}$P; product $^{31}$P NMR: δ=34.57, 33.21, 31.82 ppm; m/z=152.9, 138.9, 124.9). When the reaction was complete, the phosphonate product, a mixture of dimethyl methylphosphonate and diethyl methylphosphonate, was isolated via distillation. The distilled product was characterized via GC-MS.

EXAMPLE 3

A three-neck, 100 mL round-bottom flask, fitted with a thermometer, reflux condenser, and a septum, was charged with diphenyl phosphite (30 g, 0.13 mol). A solution of sodium methoxide (25 wt % solution in methanol, 36.9 g, 0.17 mol, 1.3 equiv. relative to phosphite) was cautiously injected dropwise while maintaining the contents of the flask at 85° C. The mixture was stirred at reflux while monitoring the reaction progress via NMR ($^1$H and $^{31}$P; product $^{31}$P NMR: δ=34.99 ppm; m/z=124.9). When the reaction was complete, the phosphonate product, dimethyl methylphosphonate, was isolated via distillation. The distilled product was characterized via GC-MS.

EXAMPLE 4

A three-neck, 100 mL round-bottom flask, fitted with a thermometer, reflux condenser, and a septum, was charged with diethyl phosphite (20 g, 0.14 mol). A solution of sodium ethoxide (21 wt % solution in ethanol, 46.9 g, 0.14 mol) was cautiously injected dropwise while maintaining the contents of the flask at 85° C. The mixture was stirred at reflux while monitoring the reaction progress via NMR ($^1$H and $^{31}$P; product $^{31}$P NMR: δ=35.51 ppm). When the reaction was complete, the phosphonate product, diethyl ethylphosphonate, was isolated via distillation. The distilled product was characterized via GC-MS.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention may comprise, consist, or consist essentially of the materials and/or procedures recited herein.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent or other publication or published document referred to in any portion of this specification is incorporated in tow into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

The invention claimed is:

1. A process for the preparation of a dihydrocarbyl hydrocarbonphosphonate, which process comprises forming a reaction mixture from components consisting of
   (i) at least one dihydrocarbyl phosphite,
   (ii) at least one alkali metal hydrocarbyloxide, and
   (iii) at least one alcohol, in an inert environment, so that a dihydrocarbyl hydrocarbonphosphonate is formed.

2. A process as in claim 1 which has at least one of the following features:
   component (i) is a dihydrocarbyl phosphite in which the hydrocarbyl groups are the same as each other;
   component (i) is at least one dihydrocarbyl phosphite in which the hydrocarbyl groups are alkyl groups.

3. A process as in claim 1 wherein the alkyl groups of component (i) have one to about six carbon atoms.

4. A process as in claim 1 wherein component (i) is dimethyl phosphite or diethyl phosphite.

5. A process as in claim 1 wherein component (ii) is at least one alkali metal hydrocarbyloxide in which the hydrocarbyl group is an alkyl, alkenyl, or aralkyl group and the alkali metal is sodium or potassium.

6. A process as in claim 1 wherein component (ii) is at least one alkali metal hydrocarbyloxide in which the hydrocarbyl group is an alkyl or alkenyl group having one to about six carbon atoms, or an aralkyl group having seven to about fifteen carbon atoms, and the alkali metal is sodium or potassium.

7. A process as in claim 1 wherein component (ii) is sodium methoxide, sodium ethoxide, or sodium benzoxide.

8. A process as in any one of claims 1-7 wherein component (iii) is at least one liquid alcohol.

9. A process as in claim 1 or 7 wherein component (iii) is methanol, ethanol, or benzyl alcohol.

10. A process as in any one of claims 1-6 wherein component (ii) is an alkali metal hydrocarbyloxide in which the alkali metal constituent is sodium and the hydrocarbyl group is an alkyl group.

11. A process as in claim 1 wherein the dialkyl phosphite is dimethyl phosphite, wherein the alkali metal hydrocarbyloxide is sodium methoxide, and wherein the alcohol is methanol.

12. A process as in claim 1 wherein the dialkyl phosphite is diethyl phosphite, wherein the alkali metal hydrocarbyloxide is sodium ethoxide, and wherein the alcohol is ethanol.

13. A process for the preparation of a dihydrocarbyl hydrocarbonphosphonate, which process comprises forming a reaction mixture from components comprising
   (i) at least one dihydrocarbyl phosphite,
   (ii) at least one alkali metal hydrocarbyloxide, and
   (iii) at least one alcohol,
   in an inert environment, so that a dihydrocarbyl hydrocarbonphosphonate is formed, wherein the mole ratio of alkali metal hydrocarbyloxide to dihydrocarbyl phosphite is in the range of about 0.9:1 to about 1.5:1, and/or wherein the alkali metal hydrocarbyloxide is present is an amount of 10 wt % to about 30 wt % based on the total weight of the alcohol and alkali metal hydrocarbyloxide.

* * * * *